US006235957B1

(12) United States Patent
Choudhury

(10) Patent No.: US 6,235,957 B1
(45) Date of Patent: May 22, 2001

(54) PROCESS FOR THE PREPARATION OF CYCLOPROPYLACETYLENE

(75) Inventor: Anusuya Choudhury, Landenberg, PA (US)

(73) Assignee: DuPont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 09/340,740

(22) Filed: Jun. 28, 1999

Related U.S. Application Data

(60) Provisional application No. 60/090,978, filed on Jun. 29, 1998.

(51) Int. Cl.$^7$ .................................................. C07C 2/00
(52) U.S. Cl. ............................. 585/538; 585/534
(58) Field of Search ...................... 585/538, 534

(56) References Cited

U.S. PATENT DOCUMENTS

| | | | |
|---|---|---|---|
| 3,865,888 * | 2/1975 | Akutagawa et al. | 260/666 A |
| 5,250,540 | 10/1993 | Arlt et al. | 514/302 |
| 5,318,988 | 6/1994 | Schohe-Loop et al. | 514/458 |
| 5,407,599 | 4/1995 | De Meijere et al. | 252/299 |
| 5,468,882 | 11/1995 | Schohe-Loop et al. | 549/407 |
| 5,663,467 | 9/1997 | Thompson et al. | 585/359 |
| 6,028,237 * | 2/2000 | Parsons, Jr. et al. | 585/359 |

FOREIGN PATENT DOCUMENTS

| | | |
|---|---|---|
| 0847974 | 6/1998 | (EP). |
| 9622955 | 8/1996 | (WO). |
| 9637457 | 11/1996 | (WO). |

OTHER PUBLICATIONS

Craig et al., Angew. Chem. Int. Ed. Engl., (1969), 8(6), 429–437.

Schoberth and Hanack, Synthesis (1972), (12), 703 No English.

Taguchi et al., J. Am. Chem. Soc., (1974), 96(9), 3011.

Wong and Ho, Synthetic Communications, (1974), 4(1), 25–27.

Villieras et al., Synthesis, (1975), 458–461.

Tsuji et al., Chemistry Letters, (1979), 481–482.

Van Hijfte et al., Tetrahedron Letters, (1989), 30(28) 3655–3656.

Corey et al., Tetrahedron Letters, (1992), 33(24), 3435–3438.

Grandjean et al., Tetrahedron Letters, (1994), 35(21), 3529–3530.

Thompson et al., Tetrahedron Letters, (1995), 36(49), 8937–8940.

Ihara et al., Tetrahedron, (1995), 51(36), 9873–9890.

Bunnage and Nicolaou, Angew. Chem. Int. Ed. Engl., (1996), 35(10), 1110–1112.

Carl Bernard Ziegler, Jr., Syhthesis and Mechanistic Studies of Polyunsaturated Fatty Acid Hydroperoxides Involving a Novel Vinylcyclopropyl Bromide Ring., Ph.D. Dissertation, Duke University (1981), 139 pp.

* cited by examiner

Primary Examiner—Jerry D. Johnson
Assistant Examiner—Thuan D. Dang

(57) ABSTRACT

The present invention relates generally to novel methods for the synthesis of cyclopropylacetylene which is an essential reagent in the asymmetric synthesis of (S)-6-chloro-4-cyclopropylethynyl-4-trifluoromethyl-1,4-dihydro-2H-3,1-benzoxazin-2-one; a useful human immunodeficiency virus (HIV) reverse transcriptase inhibitor.

14 Claims, No Drawings

PROCESS FOR THE PREPARATION OF CYCLOPROPYLACETYLENE

This application claims the benefit of U.S. Provisional Application Ser. No. 60/090,978, filed Jun. 29, 1998.

FIELD OF THE INVENTION

The present invention relates generally to novel methods for the synthesis of cyclopropylacetylene which is an essential reagent in the asymmetric synthesis of (S)-6-chloro-4-cyclopropylethynyl-4-trifluoromethyl-1,4-dihydro-2H-3,1-benzoxazin-2-one; a useful human immunodeficiency virus (HIV) reverse transcriptase inhibitor.

BACKGROUND OF THE INVENTION

Reverse transcription is a common feature of retrovirus replication. Viral replication requires a virally encoded reverse transcriptase to generate DNA copies of viral sequences by reverse transcription of the viral RNA genome. Reverse transcriptase, therefore, is a clinically relevant target for the chemotherapy of retroviral infections because the inhibition of virally encoded reverse transcriptase would interrupt viral replication A number of compounds are effective in the treatment the human immunodeficiency virus (HIV) which is the retrovirus that causes progressive destruction of the human immune system with the resultant onset of AIDS. Effective treatment through inhibition of HIV reverse transcriptase is known for both nucleoside based inhibitors, such as azidothymidine, and non-nucleoside based inhibitors. Benzoxazinones have been found to be useful non-nucleoside based inhibitors of HIV reverse transcriptase. The (S)-6-chloro-4-cyclopropylethynyl-4-trifluoromethyl-1,4-dihydro-2H-3,1-benzoxazin-2-one of formula (VI):

(VI)

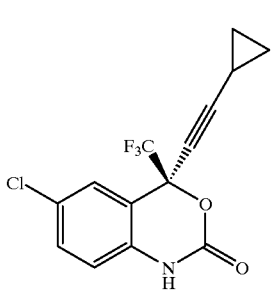

is not only a highly potent reverse transcriptase inhibitor, it is also efficacious against HIV reverse transcriptase resistance. Due to the importance of (S)-6-chloro-4-cyclopropylethynyl-4-trifluoromethyl-1,4-dihydro-2H-3,1-benzoxazin-2-one as a reverse transcriptase inhibitor, economical and efficient synthetic processes for its production need to be developed.

Cyclopropylacetylene is an important reagent in the synthesis of compound (VI). Thompson et al, *Tetrahedron Letters* 1995, 36, 937–940, describe the asymmetric synthesis of an enantiomeric benzoxazinone by a highly enantioselective acetylide addition followed by cyclization with a condensing agent to form the benzoxazinone shown below. As a reagent the cyclopropylacetylene was synthesized in a 65% yield by cyclization of 5-chloropentyne with n-butyllithium at 0°–80° C. in cyclohexane followed by quenching with ammonium chloride. The process generates a low yield of cyclopropylacetylene which is not feasible for the large commercial process of a difficult to handle reagent.

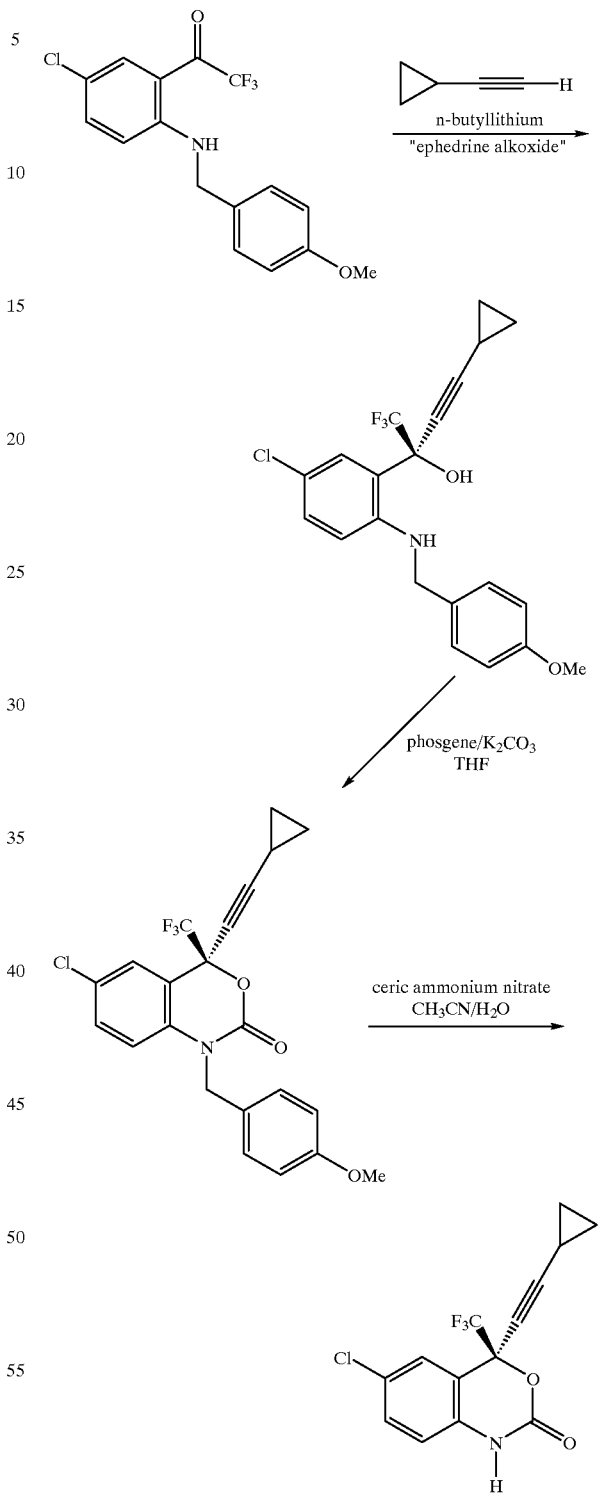

Thompson et al, PCT International Patent Application Number WO 9622955 A1 describe an improved synthesis of cyclopropylacetylene useful in the synthesis of (S)-6-chloro-4-cyclopropylethynyl-4-trifluoromethyl-1,4-dihydro-2H-3,1-benzoxazin-2-one. Application WO 9622955 A1 discloses methods which continue to be inefficient in the overall synthesis on a kilogram scale for which this invention makes significant improvements.

The majority of the cyclopropylacetylene preparations in the chemical literature teach the conversion of cyclopropylmethyl ketone to cyclopropylacetylene in a two or three step process on a bench top scale. The processes, via the following chemical scheme, teach the preparation of gem-dichloride first followed by subsequent heating to produce cyclopropylacetylene. The method will produce cyclopropylacetylene on small scale, <1 kilogram, but is not amenable for bulk production; thus an alternative needed to be developed.

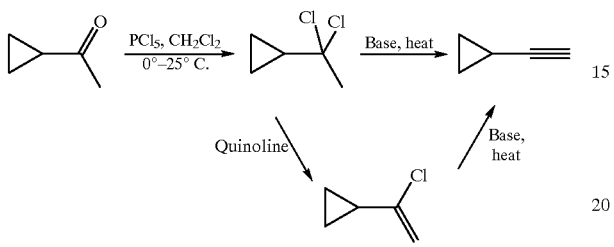

The above methods for the synthesis of cyclopropylacetylene use multistep processes with incomplete conversions and low yields; such processes render the overall synthesis inefficient and yield cyclopropylacetylene of lower purity. Thus, it is desirable to discover new synthetic routes to cyclopropylacetylene on a large scale which improve upon these limitations and provide higher yields of desired cyclopropylacetylene.

The present invention provides for essentially a one step process wherein the premixing of the reducing agent, eg. $PCl_5$, with the complexing agent, eg. quinoline, followed by addition of the cyclopropylmethylketone unexpectedly produces cyclopropylacetylene in high yield without quantitative generation of gem-dichlorides or vinylchlorides. Without premixing the reducing agent and the complexing agent, gem-dichlorides or vinylchlorides are produced as the major product. Additionally, the direct conversion of cyclopropylmethylketone to cyclopropylacetylene is affected by the chemical nature of the complexing agent. Furthermore, under harsh conditions, eg. higher refluxing temperatures, undesirable chlorination of the cyclopropyl ring occurs.

The present invention discloses a novel scalable procedure for the preparation of cyclopropylacetylene. The invention provides novel chemistry for the production of cyclopropylacetylene from cyclopropylmethylketone. The one pot reaction on a large scale occurs in high yield using convenient reaction conditions. The process provides a high solution yield (>90%) for the convenient reaction of a homogeneous mixture of phosphorous pentachloride and quinoline with cyclopropyl methyl ketone. Improvements over previously disclosed preparations of cyclopropylacetylene are the one pot reaction, scalability, essentially one step, operationally uncomplicated, isolation is uncomplicated, and produces a neat material in high purity. The final preparation of cyclopropylacetylene enables the manufacturer to circumvent the process step of dehydrohalogenation from cyclopropyl vinyl halide. Furthermore, the preparation of cyclopropylacetylene proceeds directly to high yields and suitable purities wherein the cyclopropylacetylene produced can be stored or used as a solution in an inert solvent.

None of the above-cited references describe the methods of the present invention for the synthesis of cyclopropylacetylene.

SUMMARY OF THE INVENTION

The present invention concerns an improved process suitable for the large scale preparation of substituted acetylenes, more specifically, cyclopropylacetylene. In the one pot process, phosphorous pentachloride and quinoline are premixed to form a "$PCl_5$/quinoline" mixture upon which cyclopropyl methyl ketone is contacted with the "$PCl_5$/quinoline" mixture to form cyclopropyl acetylene quantitatively. This improvement provides for high conversion of inexpensive, readily available starting materials directly to cyclopropylacetylene on an industrial scale; it enables a manufacturer to avoid the process step of dehydrohalogenation of cyclopropyl vinyl halides; and provides for high yields and suitable purities wherein the cyclopropylacetylene produced can be stored or used as a solution in an inert solvent.

DETAILED DESCRIPTION OF THE INVENTION

[1] In a first embodiment, the present invention provides a process for the preparation of a compound of formula (I), $$R^1 \equiv\!\!\equiv\!\!\equiv R^3 \qquad (I)$$

wherein:
$R^1$ is selected from:
  $C_{1-6}$ alkyl substituted with 1–3 $R^4$,
  $C_{2-6}$ alkenyl substituted with 0–1 $R^4$,
  $C_{3-7}$ cycloalkyl substituted with 0–2 $R^5$,
  phenyl substituted with 0–2 $R^6$, and
  $C_{3-6}$ carbocyclic ring substituted with 0–2 $R^5$;
$R^3$ is H, methyl, ethyl, or propyl;
$R^4$, at each occurrence, is selected from $OR^7$, F, Cl, Br, I, $NR^7R^{7a}$, phenyl, and cyclopropyl;
$R^5$, at each occurrence, is selected from D, methyl, ethyl, propyl, methoxy, ethoxy, propoxy, F, Cl, Br, and I;
$R^6$, at each occurrence, is selected from methyl, ethyl, propyl, methoxy, ethoxy, propoxy, F, Cl, Br, I, CN, and $NR^7R^{7a}$;
$R^7$ and $R^{7a}$ are independently selected from methyl, ethyl, propyl, and butyl;
said process comprising:
  (1) contacting a reducing agent with a complexing agent in a suitable nonaqueous solvent at a temperature below 20° C.;
  (2) contacting a compound of formula (II);

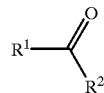

(II)

wherein $R^2$ is methyl, ethyl, propyl or butyl;
with the solution of step (1) while maintaining the temperature below 20° C. to form a compound of formula (I).

[2] In a preferred embodiment, the present invention provides a process for the preparation of cyclopropylacetylene said process comprising:
  (1) contacting a reducing agent with a complexing agent in a suitable nonaqueous solvent at a temperature below 20° C.;
  (2) contacting cyclopropylmethylketone with the solution of step (1) while maintaining the temperature below 20° C. to form cyclopropylacetylene.

[3] In a preferred embodiment the reducing agent is phosphorous pentachloride.

[4] In an another preferred embodiment the complexing agent is quinoline.

[5] In an another preferred embodiment, the nonaqueous solvent is selected from heptane, octane, nonane, decane, dodecane, toluene, xylene, chlorobenzene, pyridine, and quinoline.

[6] In a more preferred embodiment the nonaqueous solvent is dodecane.

[7] In a second embodiment, the present invention provides a process for the preparation of cyclopropylacetylene comprising:

(1) contacting phosphorous pentachloride with quinoline in a nonaqueous solvent at a temperature below 20° C.;

(2) contacting cyclopropylmethylketone with the solution of step (1) while maintaining the temperature below 20° C. to form cyclopropylacetylene.

[8] In a preferred embodiment the solvent is selected from heptane, octane, nonane, decane, dodecane, toluene, xylene, chlorobenzene, pyridine, and quinoline.

[9] In a more preferred embodiment the solvent is dodecane.

[10] In a third embodiment, the present invention provides a process for the preparation of cyclopropylacetylene comprising:

(1) contacting at least two equivalents of phosphorous pentachloride with at least three equivalents of quinoline in a nonaqueous solvent at a temperature below 20° C.;

(2) contacting one equivalent of cyclopropylmethylketone with the solution of step (1) while maintaining the temperature below 20° C. to form cyclopropylacetylene.

[11] In a fourth embodiment, the present invention provides a process for the preparation of cyclopropylacetylene comprising:

(1) contacting a reducing agent with a completing agent in a suitable nonaqueous solvent at a temperature below 20° C.;

(2) contacting cyclopropylmethylketone with the solution of step (1) while maintaining the temperature below 20° C. to form cyclopropylacetylene; and (3) isolating the cyclopropylacetylene formed.

[12] In a preferred embodiment isolating the cyclopropylacetylene formed is performed by distillation.

[13] In a more preferred embodiment isolating the cyclopropylacetylene formed is performed by vacuum distillation.

[14] In an another preferred embodiment isolating the cyclopropylacetylene formed is performed by filtering the solution of step (2) followed by distillation of the filtrate.

[15] In an another preferred embodiment isolating the cyclopropylacetylene formed is performed by (i) centrifuging the solution of step (2); (ii) decanting the supernatant; and (iii) purifying the cyclopropylacetylene by distillation.

The processes of the present invention are useful for the preparation acetylenes, and more specifically, cyclopropylacetylene, an essential intermediate in the synthesis of (S)-6-chloro-4-cyclopropylethynyl-4-trifluoromethyl-1,4-dihydro-2H-3,1-benzoxazin-2-one, which is useful as a human immunodeficiency virus (HIV) reverse transcriptase inhibitor, and compounds which are useful intermediates in the synthesis of (S)-6-chloro-4-cyclopropylethynyl-4-trifluoromethyl-1,4-dihydro-2H-3,1-benzoxazin-2-one. Such HIV reverse transcriptase inhibitors are useful for the inhibition of HIV and the treatment of HIV infection. Such HIV reverse transcriptase inhibitors are useful for the inhibition of HIV in an ex vivo sample containing HIV or expected to be exposed to HIV. Thus, such HIV reverse transcriptase inhibitors may be used to inhibit HIV present in a body fluid sample (for example, a body fluid or semen sample) which contains or is suspected to contain or be exposed to HIV. Such HIV reverse transcriptase inhibitors are also useful as standards or reference compounds for use in tests or assays for determining the ability of an agent to inhibit viral replication and/or HIV reverse transcriptase, for example in a pharmaceutical research program. Thus, such HIV reverse transcriptase inhibitors may be used as a control or reference compound in such assays and as a quality control standard.

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products within the specified temperature limits at which the reactions are carried out, i.e., temperatures which may range from the solvent's freezing temperature to the solvent's boiling temperature, unless the purpose of the solvent is to quench the reaction. A given reaction may be carried out in one solvent or a mixture of more than one solvent. Depending on the particular reaction step, suitable solvents for a particular reaction step may be selected independent of any other reaction step.

Suitable halogenated solvents include chlorobenzene, dichloromethane, chloroform, carbon tetrachloride, dichlorobenzene, dichloroethane, and trichloroethane.

Suitable ether solvents include: tetrahydrofuran, diethyl ether, ethylene glycol dimethyl ether, ethylene glycol diethyl ether, diethylene glycol dimethyl ether, diethylene glycol diethyl ether, triethylene glycol dimethyl ether, or t-butylmethyl ether.

Suitable hydrocarbon or aromatic solvents include: benzene, cyclohexane, pentane, hexane, toluene, cycloheptane, methylcyclohexane, heptane, ethylbenzene, m-xylene, o-xylene, p-xylene, octane, indane, nonane, decane, dodecane, naphthalene and mesitylene(s).

As used herein, the term "complexing agent" refers to any agent which in complex with the reducing agent effects the formation of cyclopropylacetylene from cyclopropylmethyl ketone. Examples of complexing agents include, but are not limited to, tertiaryamines and aromatic amines such as: pyridine, 2,4,6-collidine, N-methylmorpholine, 1,4-diazabicyclo[2.2.2]octane (DABCO), 1,8-diazabicyclo [5.4.0]undecene (DBU), N,N-dimethylaminopyridine(s), quinoline, methylquinoline, and N,N-diethylaniline.

As used herein, the term "reducing agent" refers to any agent which in complex with the complexing agent effects the formation of cyclopropylacetylene from cyclopropylmethyl ketone. Examples of reducing agents include, but are not limited to, phosphorous pentachloride, phosphorous pentabromide, and phosphorous trichloride in the presence of chlorine.

As used herein, the term "quenching agent" refers to any agent which eliminates the reactivity of the reducing agent or products or the reducing agent, such as $POCl_3$ or $PCl_5$, from solution. Examples of quenching agents include, but are not limited to, aqueous quenching agents; such as alkaline hydroxides (KOH, NaOH, LiOH); and nonaqueous quenching agents; such as, diaminocyclohexane.

As used herein, "alkyl" is intended to include both branched and straight-chain saturated aliphatic hydrocarbon groups having the specified number of carbon atoms; for example, "$C_{1-6}$ alkyl" denotes alkyl having 1 to 6 carbon atoms, ie. methyl, ethyl, propyl, butyl, pentyl, hexyl, and branched isomers therin. Examples of alkyls include, but are not limited to, methyl, ethyl, n-propyl, i-propyl, n-butyl, i-butyl, s-butyl, t-butyl, i-pentyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). For example "$C_{1-3}$ haloalkyl" includes, but is not limited to, trifluoromethyl, trichloromethyl, pentafluoroethyl, pentachloroethyl, heptafluoropropyl, and heptachloropropyl. "Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, cyclopentyl, or cyclohexyl. "Alkenyl" is intended to include hydrocarbon chains of either a straight or branched configuration and one or more unsaturated carbon-carbon bonds which may occur in any stable point along the chain, such as ethenyl, propenyl, butenyl and the like. As used herein, "carbocycle" or "carbocyclic residue" is intended to mean any stable 3- to 7-membered monocyclic or bicyclic carbon ring, which may be saturated or partially unsaturated. Examples of such carbocyles include, but are not limited to, cyclopropyl, cyclopentyl, cyclohexyl, cyclopentenyl, cyclohexenyl, cyclohexadienyl, and phenyl.

The present invention is contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

Synthesis

It is the object of the present invention to provide an improved process for the synthesis of cyclopropylacetylene which is useful in the synthesis of benzoxazinones which are useful as HIV reverse transcriptase inhibitors. The methods of the present invention, by way of example and without limitation, may be further understood by reference to Scheme 1. Scheme 1 details the general synthetic method for synthesis of cyclopropylacetylene. However, it is understood that the scope of the invention is not limited to preparation of cyclopropylacetylene from cyclopropylmethylketone but applicable to a broader scope. The scope of the invention as described in Scheme 1 can be practiced on a broader scope of ketone starting materials stable to conditions of the process, such as, but not limited to, phenyl methyl ketone, hexenyl methyl ketone, hexyl methyl ketone, hexyl ethyl ketone, and so forth.

Scheme 1

Step 1:

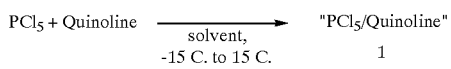

Step2:

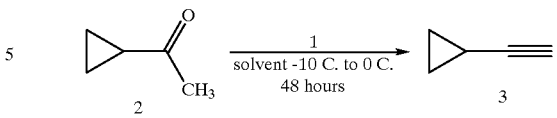

Step 1: Premixture: Preparation of Reducing Agent/Complexing Agent Complex.

This step is conducted by pre-mixing one equivalent of reducing agent in a suitable nonaqueous solvent at a suitable temperature with at least one equivalent of complexing agent to form a reducing agent/complexing agent mixture. By way of general guidance, phosphorous pentachloride is contacted with at least 1 molar equivalent of quinoline in a suitable nonaqueous solvent, under low temperature conditions to dissolve the reactants into a uniform mixture and form a "$PCl_5$/quinoline" complex.

Suitable nonaqueous solvents are nonprotic and noncarbonyl in nature, preferably hydrocarbon, ether, halogenated hydrocarbon, or aromatic solvents, in which the reducing agent and the complexing agent are soluble. The suitable solvent may be a single solvent or a mixture of solvents. These would include, but are not limited to, pentane, hexane, heptane, octane, nonane, decane, dodecane, toluene, xylene(s), benzene, mesitylene(s), t-butylmethyl ether, dialkyl ethers (ethyl, butyl), diphenyl ether, chlorobenzene, methylene chloride, chloroform, carbon tetrachloride, acetonitrile, dichlorobenzene, dichloroethane, trichloroethane, and pyridine. Preferred nonaqueous solvents are dodecane, heptane and toluene; most preferred is dodecane.

Alternatively, the suitable solvent may be the same as the complexing agent. Examples of such are quinoline and pyridine.

Suitable temperature for the premixture reaction is freezing point of solution to room temperature, a condition readily determined by one skilled in the art of organic synthesis. It is preferred to run the reaction below 20° C., more preferably at about –15° C. to about 15° C. It is even more preferable to run the reaction at about –5° C., to 0° C.

A preferred reducing agent for Step (1) is phosphorous pentachloride.

Preferred complexing agents for Step (1) are tertiary amines and aromatic amines, such as quinoline, pyridine, N-methylmorpholine, and 1,8-diazabicyclo[5.4.0]undecene. Quinoline is more preferred.

It is most preferred that the atmosphere of the reaction be dry including the solvent. It is preferred that the atmosphere be inert, more preferably nitrogen.

It is understood that one skilled in the art can determine the preferred ratio of complexing agent to reducing agent for any chosen set of agents. At least one molar equivalent to an excess of complexing agent to one equivalent of reducing agent is required; an example of an excess is where the complexing agent is the solvent of the reaction. Preferred is about 1.5 to about 10 equivalents. More preferred is about 2.0 to about 5 equivalents. Even more preferred is about 2.5 to about 5 equivalents.

It is understood that one skilled in the art can affect the outcome of the reaction by adjusting the volume of solvent per gram of reducing agent in solution. A suitable volume of solvent per gram of reducing agent can be, but is not limited to, about 0.5 ml to about 4.0 ml. Preferably, the volume is about 0.9 to 2.0 ml. More preferably, the volume of dodecane per gram of $PCl_5$ is about 0.9 to 1.1 ml; even more preferably 1.0 to 1.03 ml.

It is understood that one skilled in the art can determine the preferred reaction time of Step 1 as dependent on temperature and nonaqueous solvent. Generally, the reaction time is about 1 to about 12 hours.

Step 2. Reduction: Preparation of substituted acetylenes.

This step comprises the reduction of a ketone of Formula (II), more specifically cyclopropyl methyl ketone, by at least one molar equivalent of a preformed "reducing agent/complexing agent" complex from the mixture of Step (1) in a suitable solvent at low temperature. By way of general guidance, cyclopropyl methyl ketone is added to a solution of at least one molar equivalent of "$PCl_5$/quinoline" in a suitable solvent at a temperature less than 20° C. in a reaction vessel fitted with a means for monitoring and controlling the reaction temperature. While agitating, cyclopropylmethyl ketone is added at such a rate that the internal temperature does not exceed 20° C. The reaction is stirred and aged for a sufficient amount of time, preferably about 8 to about 72 hours, under controlled temperature to form cyclopropylacetylene. Cyclopropylacetylene may be separated from the reaction as a stable liquid by several methods of work up as described in Step 3 below, preferably by vacuum distillation.

It is preferred to add cyclopropyl methyl ketone to the preformed reducing agent/complexing agent mixture of Step (1). Alternatively, the order of addition can be reversed.

Preferred molar equivalents of "reducing agent/complexing agent" per equivalent of ketone are about 1.2 to an excess molar equivalent. For "$PCl_5$/quinoline", 1.4 to 2.5 equivalents per equivalent of ketone is more preferred; even more preferable is 1.5 to 2.0 equivalents of "$PCl_5$/quinoline".

The suitable solvent for Step (2) is the nonaqueous solvent of Step (1).

Suitable temperature for the addition of reactants in Step (2) is freezing point of solution to 20° C., a condition readily determined by one skilled in the art of organic synthesis. It is preferred to run the addition at about −10° C. to about 15° C. It is more preferable to run the addition at about −10° C. to +5° C. It is most preferable to run the addition at −10° C. to 0° C.

Suitable temperature for the aging of the reaction in Step (2) is freezing point of solution to 0° C., more preferably at −10° C. to 0° C.; most preferably at −10° C. to −5° C.

It is most preferred that the atmosphere of the reaction be dry including the solvent. It is preferred that the atmosphere be inert, more preferably nitrogen.

It is understood that one skilled in the art can determine the preferred reaction time of Step (2) as dependent on temperature and nonaqueous solvent. Generally, the reaction time is about 0.5 to about 96 hours. It is preferred the reaction time is about 8 to about 72 hours, more preferred about 24 to about 48 hours; most preferred about 36 to about 48 hours.

It is understood that the invention encompasses the synthesis of an acetylene directly from a substituted ketone. It is also understood by one of skill in the art that the conditions of Step (2) may result in side products. For example, in the preparation of the end product cyclopropyl acetylene (CPA), side products, such as cyclopropyl vinyl chloride (CPVC), cyclopropyl ring openned side products, and unknown side products may be produced. Although these side products can be minimized, it is understood that side products such as CPVC are related substances to CPA and can be converted by known methods to CPA. However, it is not necessary to convert side products, such as CPVC, to CPA in order to practice the present invention.

Step 3. Distillation: Isolation of cyclopropylacetylene.

The methods of workup for isolating high purity cyclopropylacetylene can be performed in a number of ways. The reaction of Step (2) produces cyclopropylacetylene in the presence of side products cyclopropylvinylchloride, $POCl_3$, and quinoline hydrochloride. The simplest isolation workup is controlled distillation of cyclopropylacetylene from the reaction vessel under atmospheric conditions, more preferrable is controlled vacuum distillation. An even more preferred workup method involves the steps of:

(i) adding a hydrocarbon solvent, preferably dodecane, to the reaction solution and distilling off cyclopropylacetylene which could include measurable amounts of cyclopropylvinylchloride and $POCl_3$;

(ii) adding a quenching agent to the distillate;

(iii) redistilling to collect a second distillate of cyclopropylacetylene; and if necessary, (iv) treating the second distillate with base to convert any cyclopropylvinylchloride or related substances, into cyclopropylacetylene; and (v) redistilling the second distillate to obtain pure cyclopropylacetylene.

Preferred quenching agents for the workup of Step (3) (ii) are aqueous quenching agents; preferably aqueous KOH; more preferably 5N to 14N aqueous KOH.

A suitable "base" in step (3) (iv) refers to any base the presence of which in the reaction facilitates the synthesis of cyclopropylacetylene from cyclopropylvinylchloride or related sybstances. Suitable bases may be selected by one of skill in the art of organic synthesis. Suitable bases include, but are not limited to, inorganic bases such as alkali metal, alkali earth metal, and ammonium hydroxides and alkoxides. Suitable bases also include, but are not limited to, metal amides and alkyl lithiums. Examples of suitable bases are sodium amide, lithium diisopropylamide, sodium methoxide, potassium methoxide, potassium t-butoxide, sodium butoxide, potassium and sodium t-amyloxide, potassium hydroxide, sodium hydroxide, methyllithium, butyllithium, hexyllithium, phenyllithium, and tertiary alkylammonium hydroxides. Preferred bases for the treatment of the second distillate in step (3) (iv) are potassium t-butoxide (more preferably in DMSO), sodium butoxide (more preferably in DMSO), potassium methoxide (more preferably in methanol), and lithium diisopropylamide. It is more preferred to use potassium t-butoxide (most preferably in DMSO).

Alternatively, the quenching of $POCl_3$ in step (3) (ii) can be performed by a nonaqueous quenching agent. Preferred nonaqueous quenching agents are diaminocyclohexane.

Alternatively, the reaction solution of Step (2) can be filtered to remove all solids, in particular the quinoline hydrochloride, after which the controlled vacuum distillation or the procedure of steps (3) (i) through (3) (v) above can be performed.

Alternatively, the reaction solution of Step (2) can be centrifuged and the supernatant decanted to remove all solids, in particular the quinoline hydrochloride, after which controlled vacuum distillation or the procedure of steps (3) (i) through (3) (v) above can be performed on the decanted supernatant.

The following examples are meant to be illustrative of the present invention. These examples are presented to exemplify the invention and are not to be construed as limiting the invention's scope.

The following abbreviations are used herein:

| | |
|---|---|
| CPMK | cyclopropylmethylketone |
| CPA | cyclopropylacetylene |
| CPVC | cyclopropylvinylchloride |
| DCCP | 1,1-dichloro-1-cyclopropylethane |

The following analytical gas chromotagraphy (GC) test method was used to monitor completion of reaction and quantitation of acetylenes and side products formed.

Column: J&W DB-1, 30 m×0.32 mm I.D., 5 μm thick film;
Oven Temperature:
  50° C. for 5 min;
  50° C. to 225° C. at 20° C./min;
  225° C. for 1 minute.
Injector Temp: 250° C.
Detector Temp: 300° C.
Inlet Pressure: 8 psi.
Carrier FLow: 1.6 ml/min.
Sample Injection: solution in acetonitrile
Retention times:
  CPA: 7.7 min
  CPVC: 9.9 min.
  CPMK: 10.6 min.
  DCCP: 12.5 min
  pentyne: 6.7 min
  5-chloro-1-pentyne: 11.1 min.

EXAMPLE 1

Preparation of Cyclopropylacetylene

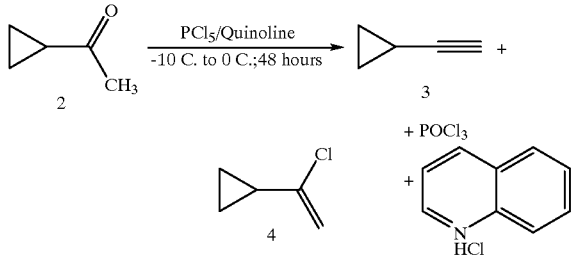

A 4-neck 500 mL jacketed reactor with provision for heating and cooling, equipped with $N_2$-inlet, thermocouple, air stirrer and addition funnel was flushed with nitrogen for 15 minutes and nitrogen atmosphere was maintained throughout the reaction. Dodecane (156 mL) was charged to the reactor and stirred. The reactor was cooled to 1° C. Finely ground $PCl_5$ (156 gm, 0.75 mol, 1.5 equivalent, 98%) was charged to the reactor between 1 to 5° C. (3 minutes) with constant stirring. Quinoline (156 g, 1.25 mol, 2.5 equivalent) was charged to the stirring slurry between 0 to 5° C. The mixture was aged at 0° C. for 0.5 h and cooled to −5° C. Neat cyclopropylmethylketone (2, 50 mL, 1 equivalent, 0.5 mol) was charged to the reactor between −5 to −3° C. The reaction mixture was stirred at −3° C. for 15 h and 20° C. for 4 h. GC analysis of the reaction mixture shows a 95% complete reaction. The reaction mixture was filtered through a pressure filter, the solids were washed with 3×50 mL dodecane (9243 gm filtrate and 264.8 gm solids). The filtrate was quenched with 300 mL of 15N KOH solution (by slowly adding the filtrate to KOH) between 0 to 15° C. (1 h). The aqueous layer was extracted with 50 mL of dodecane. The combined organics were dried over 19.4 g $Na_2SO_4$. Organic layer 200 g. (8.8 g CPA 3, 14.8 g CPVC 4, 55.6% solution yield). The organic layer was vacuum distilled at pot temp 97° C., 24–33° C. head temp, 650 mm Hg (1 h). Distillate collected 22 g.

The distillate was charged into 28 g of potassium t-butoxide (90.5 equivalent with respect to CPMK)/35 mL DMSO (1.2 mL/g K-t-BuO) at 40 to 45° C. (controlled by icebath cooling) and heated to 70° C. for 2 h. Distilled at pot temperature of 90–115° C. 90.8% pure CPA (5.7 gm). Cooled the pot to 60° C., charged 50 mL of toluene and distilled at 116–118° C. to obtain a CPA solution of 26.3% in toluene (9 g).

EXAMPLE 2

Preparation of Cyclopropylacetylene

A 4-neck 3 L jacketed reactor with provision for heating and cooling equipped with $N_2$-inlet, thermocouple, air stirrer and addition funnel was flushed with nitrogen for 15 minutes and nitrogen atmosphere was maintained throughout the reaction. Quinoline 1.6 L (1752 g, 99% pure, 13.56 mol, 9.48 equiv.) was charged to the reactor. The reactor was cooled to −10° C. Finely ground $PCl_5$ 594 g (2.85 mol, >95% pure, 1.99 equiv.) was added portion wise between −1 to −10° C. with constant stirring. The mixture was stirred at 0° C. for 1 h and cooled back down to −10° C. Cyclopropylmethyl ketone (141 mL, 120 g, 1.43 mol, 1 equivalent) was added between −8 to 10° C. and the mixture was left stirring 48 h at −10° C. The mixture was warmed to +50° C. for 4 h and then warmed to ambient temperature. GC analysis shows the ratio of CPA:CPMK:CPVC/114:13:64.

The mixture was warmed to room temperature and distillation was done at 20 mm/Hg with pot temperature between 50 to 55° C., trapping the distillate in a cold trap at −78° C.

Hydrolysis of the Distillate: A 4 neck 1 L round bottom flask was equipped with air stirrer, thermometer inlet, dry-ice condensor with nirogen inlet and addition funnel. The stirring solution of KOH 65.0 g and 400 mL $H_2O$ was cooled to −5° C. Addition funnel was charged with the distillate which was charged slowly to the base solution between −5 to +15° C. The pH of the solution was maintained below 7 by adding more aqueous KOH solution. The aqueous layer was extracted with 2×25 mL of dodecane. The combined organics were dried over anhydrous $MgSO_4$ (139.76 g) and distilled in a 250 mL round bottom flask at atmospheric pressure with pot temperature between 60 to 89° C. (steady rise in temperature) to collect 44.83 g of oil. This is a mixture of cyclopropylacetylene (CPA), 3, and cyclopropylvinylchloride (CPVC), 4.

A two-neck 100 mL round bottom flask containing the above distillate with the temperature probe was equipped with a 5-plate oldershaw jacketed column(10" length). The neat CPA was collected between 49–53° C. Meanwhile, the pot temperature was between 66 to 101° C. Yield of neat CPA was 36.23 g (38% yield). A second fraction was collected between 87–93° C. (19.58 g of neat cyclopropylvinylchloride).

EXAMPLE 3

Preparation of cyclopropylacetylene

A 4-neck 5 L jacketed reactor with provision for heating and cooling equipped with $N_2$-inlet, thermocouple, air stirrer and addition funnel was flushed with nitrogen for 15 minutes and nitrogen atmosphere was maintained throughout the reaction. Quinoline 2 L (2187 gm, 99% pure, 16.9 mol, 11.9 equiv.) was charged to the reactor. The reactor was cooled to −10° C. Finely ground $PCl_5$ 742.6 g (3.56 mol, >95% pure, 2.5 equiv.) was added portion wise between −1 to −10° C. with constant stirring. The mixture was stirred at 0° C. for 1 h and cooled back down to −10° C. Cyclopropylmethyl ketone (141 mL, 120 g, 1.43 mol, 1 equivalent) was added between −8 to 10° C. and the mixture was left stirring 48 h at −10° C. GC area % analysis showed 63.8% area CPA, 24.3% area cyclopropyl vinyl chloride with 6% unreacted starting material and 5% ring openning product.

The mixture was warmed to room temperature and distillation was done at 65 mm/Hg with the distillate collecting between 24 to 59° C. (head temperature), trapping the distillate in a cold trap at −78° C. Total amount of distillate collected was 156.9 g.

The distillate was redistilled at atmospheric pressure with pot temperature starting with 52° C. and 96° C. as the final temperature. Distillates were collected between 25–58° C. Total weight of this distillate was 47.3 g.

Hydrolysis of the Distillate: A 4 neck 500 mL round bottom flask was equipped with air stirrer, thermometer inlet, dry-ice condensor with nitrogen inlet and addition funnel. The stirring solution of 56.0 g KOH and 200 mL $H_2O$ was cooled to −10° C. Addition funnel was charged with the distillate (47.3 g) and charged slowly over 30 minutes between −4 to −9° C. The strongly basic mixture was warmed to ambient temperature and layers were separated. The aqueous layer was extracted once more with 10 mL of dodecane.

The combined organics were distilled at atmospheric pressure with pot temperature between 63° C. and 90° C. and head temperature between 48 to 52° C. to give 22.26 g of neat cyclopropylacetylene with 99.55% area purity.

EXAMPLE 4

Preparation of cyclopropylacetylene

A 4-neck reactor equipped with $N_2$-inlet, thermocouple, air stirrer and addition funnel was flushed with nitrogen for 15 minutes and dodecane (10 ml) was charged. Finely ground $PCl_5$ (13.1 g, 62.9 mmol) was added portion-wise to the stirred dodecane. The mixture was cooled to −8° C. and quinoline (35 ml, 300 mmol) was charged dropwise between −8° C. and −3° C. over 5 minutes. The mixture was aged for 35 minutes at −8° C. and neat cyclopropylmethyl ketone (1.55 ml, 15.7 mmol, 1 equivalent) was added dropwise over 10 minutes. After 35 minutes the GC area % ratio of CPA to CPVC was 30:70. The mixture at this point was frozen in dryice/acetone bath overnight. The temperature next morning after 20 hours was 15° C. with a CPA:CPVC ratio of 75:25. The mixture was cooled to 1° C. and was held for 8 hours. GC analysis showed 87.3% area CPA, 12.7% area cyclopropylvinylchloride. The reactor was warmed to ambient temperature. Hexanes (5 ml) was added and CPA was distilled as a solution in hexanes (3.8 g).

EXAMPLE 5

Preparation of cyclopropylacetylene in Toluene

A slurry of $PCl_5$ 15.33 g (73.6 mmol, 2.2 equiv.) in toluene (45 mL) was cooled to −2° C. and quinoline (20 mL, 167.3 mmol, 5 equiv.) was added between −2 to −4° C. The reaction mass was stirred for 1 hour at 0° C. and was cooled to −13° C. Cyclopropyl methylketone (3.31 mL, 33.45 mmol, 1 equiv.) was added between −8 and −13° C. The mixture was stirred 3 hours at −1° C., 5.5 hours at 0° C. and then left 1 hour at ambient temperature. The analysis of the reaction mixture shows CPA:CPMK:CPVC/3.7:3:2.6.

EXAMPLE 6

Preparation of cyclopropylacetylene in Heptane

A slurry of $PCl_5$ (10.37 g, 49.8 mmol, 2.3 equiv.) in heptane (26 mL) was cooled to −2° C. and quinoline (29.5 mL, 250 mol, 11.6 equiv.) was added between −2 to −4° C. The reaction mass was stirred for 1 hour at 0° C. and was cooled to −13° C. Cyclopropyl methylketone (2.1 mL, 21.6 mmol, 1 equiv.) was added between −8 and −13° C. The mixture was stirred 3 hours at −13° C., 5.5 hours at 0° C. and then left 1 hour at ambient temperature. Solids precipitated out from the reaction mixture. The analysis of the reaction mixture shows 59.93:30.5:3.1:3:3.5/CPA:CPVC:DCCP:ring openned:unknown.

EXAMPLE 7

Preparation of cyclopropylacetylene in Chlorobenzene

A slurry of $PCl_5$ (16.8 g, 80 mmol, 2.0 equiv.) in chlorobenzene (32 mL) was cooled to −2° C. and quinoline (47 mL, 400 mmol, 10 equiv.) was added between −2 to −4° C. The reaction mass was stirred for 1 hour at 0° C. and was cooled to −13° C. Cyclopropyl methylketone (3.5 mL, 40 mmol, 1 equiv.) was added between −8 and −13° C. The mixture was stirred 3 hours at −13° C., 5.5 hours at 0° C. and then left 1 hour at ambient temperature. Solids precipitated out from the reaction mixture. The analysis of the reaction mixture shows 35.37:24.4:0.86:14.64/CPA:CPVC:ring openned:unknown.

EXAMPLE 8

Preparation of cyclopropylacetylene in m-Xylene

A slurry of $PCl_5$ (75.1 g, 0.36 mol, 2.0 equiv.) in m-xylene (145 mL) was cooled to −6° C. and quinoline (68.4 mL, 0.578 mol, 2.5 equiv.) was added between −2 to −4° C. The reaction mass was stirred for 1 hour at 0° C. and was cooled to −13° C. Cyclopropylmethylketone (23 mL, 0.23 mol, 1 equiv.) was added between −8 and −10° C. The mixture was stirred for 1 h at −10° C., 5.5 h at 0° C. and then left 1 hour at ambient temperature. Solids precipitated out from the reaction mixture. The analysis of the reaction mixture shows 25.9:5.6:56.16:7:5.1 of CPA:CPMK:CPVC:DCCP:ring openned.

EXAMPLE 9

Preparation of cyclopropylacetylene with quinoline and 1,8-diazabicyclo[5.4.0]undecene as a complexing agent A slurry of $PCl_5$ (27.1 g, 260 mmol, 2.0 equiv.) in quinoline (100 mL, 524 mmol, 8 equiv.) was prepared by adding $PCl_5$ to quinoline between 13 to 27° C. Then the mixture was cooled to −10° C. Cyclopropylmethylketone (6.5 mL, 65 mmol) was added to the mixture over 2 minutes between −6 to −10° C. 1,8-Diazabicyclo[5.4.0]undecene (20 mL, 130 mmol) was added slowly. There was an exotherm and the temperature went up to 3° C. The reactor temperature was lowered to −15° C. over 1 h. GC analysis of the reaction mass showed 30% CPA, 62% of the unreacted ketone and 7.6% cyclopropyl vinyl chloride.

EXAMPLE 10

Preparation of cyclopropylacetylene with pyridine as complexing agent

A slurry of $PCl_5$ (33.43 g, 160 mmol, 1 equiv.) in dodecane (40 mL) was made by adding finely ground $PCl_5$ to a stirring dodecane between −5 and +5° C. Pyridine (64 mL, 800 mmol, 5 equiv.) was added between 22–26° C. Then the mixture was cooled to −10° C. The mixture was stirred for 15 minutes. To the white slurry was added cyclopropylmethylketone (15.9 mL, 160 mmol) between 27 to 15° C. over 2 minutes. After 20 minutes the mixture selfheated to 71° C., solidified and stirring stopped. It was warmed to ambient temperature and the gluey solids were stirred overnight. Gc analysis of the reaction mass shows 28% CPA, 19% cyclopropylmethylketone and 42% cyclopropylvinylchloride with 6% of the ring openning product.

EXAMPLE 11

Preparation of cyclopropylacetylene with N-methylmorpholine as completing agent $PCl_5$ (44.2 g, 212 mmol, 1.5 equiv.) was added to N-methylmorpholine (69 mL, 0.672 mmol, 4.43 equiv.) around −5° C. After ageing for 1 h at 0° C., the mixture was cooled to −5° C. and stirred overnight at −5° C. The GC analysis of the reaction mass shows CPA:CPMK:CPVC/ 33%:51%:16%.

EXAMPLE 12

Preparation of cyclopropylacetylene with 2,4,6 collidine as complexing agent $PCl_5$ (5 g, 24 mmol, 2.02 equiv.) was added to dodecane (10 mL), cooled to 0° C. 2,4,6-Collidine (2.9 g, 23.73 mmol) was added dropwise. Mixture was stirred for 1 h at 0° C. and cyclopropylmethylketone (1 g, 11.89 mmol) was added to it. The mixture was stirred overnight at ambient temperature. GC analysis of the crude reaction mixture showed trace of CPA:CPMK:CPVC/40:61:46.

EXAMPLE 13

Preparation of phenylacetylene

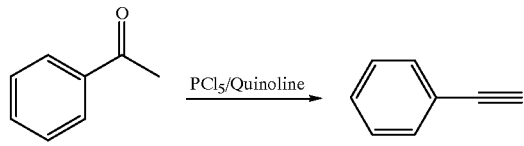

To a 125 mL 3-neck flask equipped with air-stirrer, $N_2$-inlet, thermocouple was charged dodecane(12 mL). Finely ground $PCl_5$ (22.9 g, 110 mmol, 1.51 equiv.) was added to it. Quinoline (43 mL, 363.9 mmol, 5.03 equiv.) was added between 0–5° C. The mixture was stirred for 1 h between 0–5° C. The reactor was cooled to −10° C. and acetophenone (8.7 g, 2.4 equiv.) was slowly added over 20 minutes between −5 to −10° C. The mixture was transferred to a 100 mL 2-neck reactor with magnetic stirring bar and with a distillation head. The original reactor was rinsed with 5 mL of dodecane and combined with the main. The distillation at 0.1 torr at 50° C. could not distill all the phenylacetylene. The solids were filtered from the distillation residue and washed with 10 mL of dodecane. The distillate was added to the main filtrate. Some solids dropped out overnight. Adding acetonitrile dissolved the solids and it separated in to two layers (top layer was 18.8 g and bottom layer was 68.37 g). Calculation of the solution yield shows for the phenylacetylene to be 30%.

EXAMPLE 14

Preparation of cyclohexenylacetylene

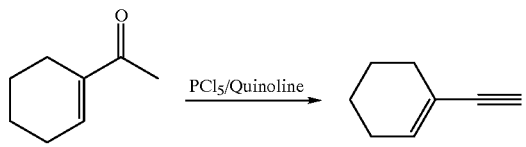

To a 125 mL 3-neck flask equipped with air-stirrer, $N_2$-inlet, thermocouple was charged dodecane(12 mL). Finely ground $PCl_5$ (22.9 g, 110 mmol, 1.51 equiv.) was added to it. Quinoline (43 mL, 363.9 mmol, 5.03 equiv.) was added between 0–5° C. The mixture was stirred for 1 h between 0–5° C. The reactor was cooled to −10° C. and 1-acetyl-1-cyclohexene (9.3 ml, 72.3 mmol, 1 equiv.) was slowly added over 20 minutes between −5 to −10° C. The reaction mixture was warmed to ambient temperature and stirred for 3.5 h. GC analysis of the reaction mixture showed a ratio of 4.6:5 of enyne to ketone. After stirring overnight, the mixture was warmed to 35° C. for 3 h, the ratio changed to 3.7:2.8. The reaction mixture was diluted with heptane (25 mL), stirred well and filtered through a coarse frit. The filtrate was dissolved in acetonitrile and calculation of the solution yield showed it to be 19%. (Retention time of the ketone, enyne and quinoline are 3.6 min., 5.1 min, and 18 min.)

EXAMPLE 15

Preparation of 1-phenyl-1-propyne

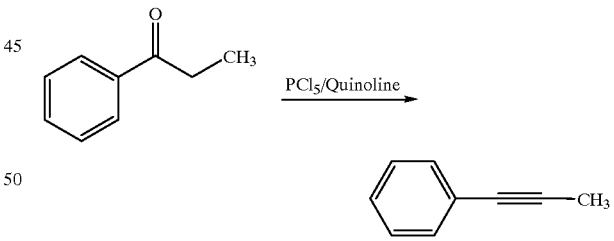

To a 125 mL 3-neck flask equipped with air-stirrer, $N_2$-inlet, thermocouple was charged dodecane(12 mL). Finely ground $PCl_5$ (22.9 g, 110 mmol, 1.51 equiv.) was added to it. Quinoline (43 mL, 363.9 mmol, 5.03 equiv.) was added between 0–5° C. The mixture was stirred for 1 h between 0–5° C. The reactor was cooled to −10° C. and propiophenone (9.7 g, 72.4 mmol, 1 equiv.) was slowly added over 20 minutes between −5 to −10° C. The reaction mixture was warmed to ambient temperature and stirred for 3 days. GC analysis of the reaction mixture showed a ratio of 7.08:1.1 of propiophenone to phenylalkyne. More dodecane was added and the mixture was quenched with aqueous NaOH. Most of it went to solution by adding ethylacetate.

Calculation of the solution yield showed the product 1-phenyl-1-propyne to be 13%.

What is claimed is:

1. A process for preparation of a compound of formula (I),

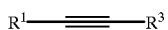
(I)

wherein:
R$^1$ is selected from the group consisting of:
- C$_{1-6}$ alkyl substituted with 1–3 R$^4$,
- C$_{2-6}$ alkenyl substituted with 0–1 R$^4$,
- C$_{3-7}$ cycloalkyl substituted with 0–2 R$^5$,
- phenyl substituted with 0–2 R$^6$, and
- C$_{3-6}$ carbocyclic ring substituted with 0–2 R$^5$;

R$^3$ is H, methyl, ethyl, or propyl;

R$^4$, at each occurrence, is selected from the group consisting of OR$^7$, F, Cl, Br, I, NR$^7$R$^{7a}$, phenyl, and cyclopropyl;

R$^5$, at each occurrence, is selected from the group consisting of D, methyl, ethyl, propyl, methoxy, ethoxy, propoxy, F, Cl, Br, and I;

R$^6$, at each occurrence, is selected from the group consisting of methyl, ethyl, propyl, methoxy, ethoxy, propoxy, F, Cl, Br, I, CN, and NR$^7$R$^{7a}$;

R$^7$ and R$^{7a}$ are independently selected from the group consisting of methyl, ethyl, propyl, and butyl;

said process comprising:
(1) contacting a reducing agent with a complexing agent in a nonaqueous solvent at a temperature below 20° C. to form a solution;
(2) contacting a compound of formula (II);

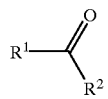
(II)

wherein R$^2$ is methyl, ethyl, propyl or butyl;
with the solution of step (1) while maintaining the temperature below 20° C. to form a compound of formula (I).

2. A process for synthesis of cyclopropylacetylene, said process comprising:
(1) contacting a reducing agent with a complexing agent in a nonaqueous solvent at a temperature below 20° C. to form a solution;
(2) contacting cyclopropylmethylketone with the solution of step (1) while maintaining the temperature below 20° C. to form a solution comprising cyclopropylacetylene.

3. The process of claim 2 wherein the reducing agent is phosphorous pentachloride.

4. The process of claim 2 wherein the complexing agent is quinoline.

5. The process of claim 2 wherein the nonaqueous solvent is selected from the group consisting of heptane, octane, nonane, decane, dodecane, toluene, xylene, chlorobenzene, pyridine, and quinoline.

6. The process of claim 2 wherein the nonaqueous solvent is dodecane.

7. A process for synthesis of cyclopropylacetylene, said process comprising:
(1) contacting phosphorous pentachloride with quinoline in a nonaqueous solvent at a temperature below 20° C. to form a solution;
(2) contacting cyclopropylmethylketone with the solution of step (1) while maintaining the temperature below 20° C. to form cyclopropylacetylene.

8. The process of claim 7 wherein the solvent is selected from the group consisting of heptane, octane, nonane, decane, dodecane, toluene, xylene, chlorobenzene, pyridine, and quinoline.

9. The process of claim 7 wherein the solvent is dodecane.

10. A process for synthesis of cyclopropylacetylene, said process comprising:
(1) contacting at least two equivalents of phosphorous pentachloride with at least three equivalents of quinoline in a nonaqueous solvent at a temperature below 20° C. to form a solution;
(2) contacting one equivalent of cyclopropylmethylketone with the solution of step (1) while maintaining the temperature below 20° C. to form cyclopropylacetylene.

11. The process of claim 2 further comprising (3) isolating the cyclopropylacetylene formed by distillation.

12. The process of claim 2 further comprising (3) isolating the cyclopropylacetylene formed by vacuum distillation.

13. The process of claim 2 further comprising (3) isolating the cyclopropylacetylene formed by filtering the solution of step (2) followed by distillation of the filtrate.

14. The process of claim 2 further comprising (3) isolating the cyclopropylacetylene formed by (i) centrifuging the solution of step (2); (ii) decanting the supernatant; and (iii) purifying the cyclopropylacetylene by distillation.

* * * * *